United States Patent [19]

Fancher

[11] 4,108,988
[45] Aug. 22, 1978

[54] INSECTICIDAL HYDRAZONE PHOSPHATES AND PHOSPHONATES

[75] Inventor: Llewellyn W. Fancher, Orinda, Calif.

[73] Assignee: Stauffer Chemical Company, Westport, Conn.

[21] Appl. No.: 812,956

[22] Filed: Jul. 5, 1977

[51] Int. Cl.² .......................... A01N 9/36; C07F 9/165
[52] U.S. Cl. ................................ 424/211; 260/455 P; 260/923
[58] Field of Search ........................... 260/455 P, 923; 424/211

[56] References Cited

U.S. PATENT DOCUMENTS 3,518,327   6/1970   Fearing ................................ 424/211

*Primary Examiner*—Anton H. Sutto
*Attorney, Agent, or Firm*—Joel G. Ackerman

[57] ABSTRACT

Compounds having the formula

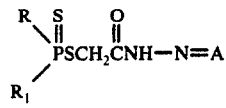

in which R is lower alkyl or lower alkoxy, $R_1$ is lower alkoxy, A is cycloalkyl, lower alkyl-substituted cycloalkenyl, or

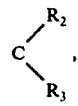

$R_2$ and $R_3$ are independently alkyl, aryl, aralkyl, cycloalkyl, hydrogen, or

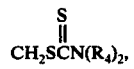

and $R_4$ is lower alkyl. Compounds of this formula have been found to possess utility as insecticides, particularly against aphids and the housefly.

26 Claims, No Drawings

INSECTICIDAL HYDRAZONE PHOSPHATES AND PHOSPHONATES

SUMMARY OF THE INVENTION

This invention relates to novel insecticidal compounds having the formula

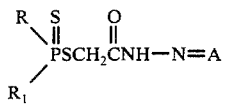

in which R is lower alkyl or lower alkoxy, $R_1$ is lower alkoxy, A is cycloalkyl, lower alkyl-substituted cycloalkenyl or

$R_2$ and $R_3$ are independently alkyl, aryl, aralkyl, cycloalkyl, hydrogen, or

and $R_4$ is lower alkyl.

By the term "alkyl" is meant such groups having from one to about 10 carbon atoms, in both straight and branched chain configurations. Preferably, the alkyl groups have from one to six carbon atoms, and most preferably from one to four. Examples of such groups are methyl, ethyl and the various propyl and butyl groups.

By the terms "lower alkyl" and "lower alkoxy" are meant such groups containing from 1 to 4 carbon atoms, such as methyl, ethyl, propyl, butyl, ethoxy, isopropoxy and the like.

A preferred embodiment of the aryl groups is phenyl. The term "aralkyl" includes radicals having both aromatic and aliphatic structures. A preferred embodiment of this group is phenethyl; benzyl is another embodiment. The term "cycloalkyl" includes such groups having from 3 to 7 carbon atoms. Preferred embodiments of this group are, for A, cyclohexyl, and for $R_2$ or $R_3$, cyclopropyl. The preferred lower alkyl-substituted cycloalkenyl group is 3,5,5-trimethylcyclohex-2-enyl.

In one embodiment, R is alkyl and $R_1$ is alkoxy; the compounds are phosphonates. At the present these compounds appear to be the most active of the group. In another embodiment R and $R_1$ are both lower alkoxy; the compounds are phosphates. In yet another preferred embodiment $R_2$ and $R_3$ are both alkyl, preferably both alkyl having from one to six carbon atoms. In still another embodiment $R_2$ is alkyl and $R_3$ is phenyl. In another embodiment, $R_2$ and $R_3$ are independently alkyl, aryl, aralkyl, cycloalkyl or

In another aspect, this invention relates to an insecticidal composition of matter comprising:

(a) an insecticidal amount of a compound having the formula

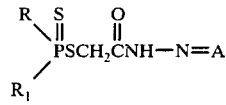

in which R is lower alkyl or lower alkoxy, $R_1$ is lower alkoxy, A is cycloalkyl, lower alkyl-substituted cycloalkenyl or

$R_2$ and $R_3$ are independently alkyl, aryl, aralkyl, cycloalkyl, hydrogen or

and $R_4$ is lower alkyl; and
(b) an inert carrier.

In yet another aspect this invention comprises a method for controlling insects comprising applying to the insect or the habitat thereof an insecticidally effective amount of a compound having the formula

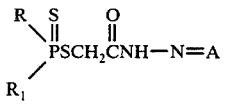

in which R, $R_1$ and A are as previously defined. Preferred embodiments of this method involve the use of preferred embodiments of the compounds of this invention and also against preferred insects, namely aphids, the housefly and mites.

In general, the compounds of the present invention can be prepared by a three-step procedure.

In the first step, an alkyl chloroacetate, such as ethyl chloroacetate, is reacted with a phosphorodithioc acid in the presence of a base, using an appropriate solvent:

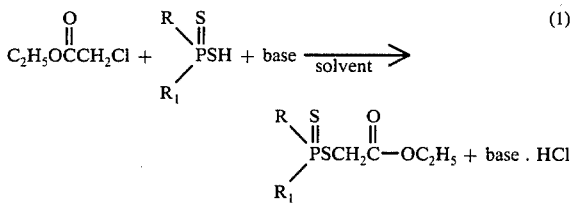

(1)

Temperature of this step can be from about 25° C. to about 80° C. As the base there may be utilized a tertiary amine, such as triethylamine. Alternatively, a sodium or potassium salt of the dithiophosphoric or — phosphonic acid may be used without requiring an additional base. Suitable solvents include benzene, chloroform, ketones, and esters.

In the second step, the product of step 1 is reacted with hydrazine (conveniently used as hydrazine hydrate):

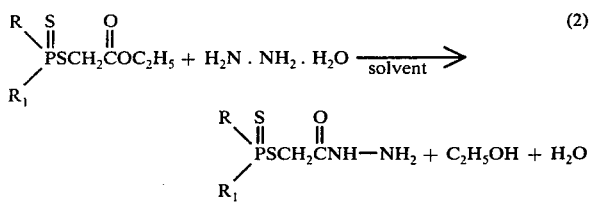

Temperatures for this reaction can be from about 0° C. to about 85° C. The reaction is conducted in the presence of a solvent, preferably an alcohol such as ethanol.

In the third step, the product of reaction (2) is reacted with an aldehyde or ketone to produce the final hydrazone product:

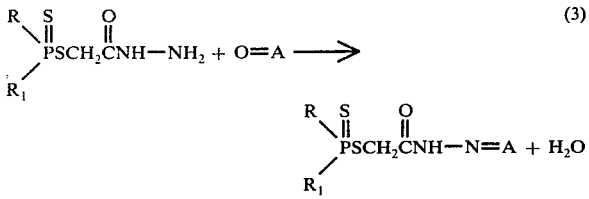

This condensation reaction can be carried out by refluxing the mixture in the presence of an alcohol or a water-insoluble solvent such as benzene, with the water of reaction being removed by azeotropic distillation. The product can then be recovered by evaporation of the solvent.

The following constitute representative examples of preparation of compounds of the above invention and intermediates therefor.

EXAMPLE 1

Preparation of O,O-diethylphosphorodithioyl-S-acethydrazide intermediate

In a flask cooled to below 30° C. were placed 22.3 g. (0.12 mole) O,O-diethylphosphorodithioic acid, 25 ml. benzene and 12.1 g. (0.12 mole) triethylamine; an additional quantity of triethylamine was then added to bring the pH of the mixture to 7.5. There was then added 12.3 g. (0.1 mole) ethyl chloroacetate; the mixture was stirred at ambient temperature for one hour, then refluxed for 4 hours. After cooling, the resulting product was washed twice with 200 ml. portions of dilute aqueous sodium chloride, then dried over anhydrous $MgSO_4$, filtered and the solvent removed under vacuum. There was obtained 24.7 g. of O,O-diethylphosphorodithioyl ethyl acetate, a non-viscous liquid, $n_D^{30}$ 1.4966.

The product obtained above was dissolved in 35 ml. ethanol and 4.6 g. (0.091 mole) hydrazine hydrate was added with cooling below 10° C. The mixture was let stand at ambient temperature for several hours, then heated under reflux on a steam bath for 2 hours. The ethanol and other volatiles were stripped under vacuum to yield 23.2 g. (98% of theoretical) of the desired hydrazide, a nearly colorless liquid, $n_D^{30}$ 1.5463.

EXAMPLE 2

Preparation of Ethyl, O-isopropyl phosphorodithioyl-S-acethydrazide intermediate This intermediate was prepared similarly to the intermediate of Example 1, starting with 44.2 g. (0.24 mole) ethyl, O-isopropylphosphorodithioic acid, 24.2 g. (0.24 mole) triethylamine and 24.6 g. (0.2 mole) ethyl chloroacetate. The product, ethyl, O-isopropylphosphorodithioyl-ethyl acetate was reacted with 8.65 g. (0.173 mole) hydrazine hydrate to yield 44.4 g. (86.7% of theoretical) of the corresponding acethydrazide, a light orange liquid, $n_D^{30}$ 1.5457.

EXAMPLE 3

Preparation of O,O-diethylphosphorodithioyl-acethydrazideacetone hydrazone (Compound 1 in Table I)

In a flask were mixed 7.7 g. (0.03 mole) O,O-diethylphosphorodithioyl-S-acethydrazide (as prepared in Example 1), 2.9 g. (0.05 mole) acetone and 35 ml. ethanol. The mixture was refluxed for 2.5 hours on a steam-bath, then evaporated under vacuum. The crude product was mixed with benzene, dried over $MgSO_4$, filtered and evaporated under vacuum. There was obtained 7.9 g. (88.7% of theoretical) of product, $n_D^{30}$ 1.5329. The structure of this compound was confirmed by infra-red spectral analysis.

EXAMPLE 4

Preparation of Ethyl, O-isopropylphosphorodithioylacethydrazide-acetone hydrazone (Compound 4 in Table I)

Using the same procedure as in Example 3, from 5.12 g. (0.02 mole) ethyl, O-isopropylphosphorodithioyl-S-acethydrazide (prepared as in Example 2), 2.32 g. (0.04 mole) acetone and 25 ml. ethanol, there was obtained 5.0 g. (84.4% of theoretical) of the desired product, a light yellow liquid, $n_D^{30}$ 1.5392. The structure of the compound was confirmed by infra-red spectral and mass spectral analysis.

EXAMPLE 5

Preparation of Ethyl, O-isopropylphosphorodithioylacethydrazide-methyl isobutyl ketone hydrazone (Compound 6 in Table I)

In a flask were mixed 5.012 g. (0.02 mole) ethyl, O-isopropylphosphorodithioyl-S-acethydrazide, 2.0 g. (0.02 mole) methyl isobutyl ketone and 100 ml. benzene. The mixture was stirred and refluxed for 2 hours. Water which was formed was removed azeotropically with a Dean-Stark tube. After removal of volatile substances in a rotary evaporator there was obtained 6.69 g. (99% of theoretical) of the desired product, a yellow liquid $n_D^{30}$ 1.5246. Structure of the compound was confirmed by nmr (nuclear magnetic resonance) analysis.

EXAMPLE 6

Preparation of Ethyl, O-isopropyldithioylacethydrazidecyclohexanone hydrazone (Compound 27 in Table I)

Using the same procedure as in Example 3, starting with 5.12 g. (0.02 mole) ethyl, O-isopropylphosphorodithioyl-S-acethydrazide, 1.96 g. (0.02 mole) cyclohexanone and 50 ml. ethanol there was produced 6.10 g. (90.8% of theoretical) of the desired product, a yellow liquid, $n_D^{30}$ 1.5506. The structure was confirmed by nmr (nuclear magnetic resonance) analysis.

EXAMPLE 7

Preparation of Ethyl, O-ethylphosphonodithioyl acethydrazide-N,N-dimethyldithiocarbanylacetone hydrazone (Compound 23 in Table 1).

In a flask, 57.3 g. (0.32 mole) sodium N,N-diethyldithiocarbamate dihydrate was slurred in 150 ml. acetone. The temperature was maintained at 25° C. Then, 27.8 g. (0.03 mole) monochloroacetone was added, with stirring. The temperature rose rapidly to 55° C. The mixture was stirred and refluxed for 0.5 hours, filtered while warm, and the solids washed several times with acetone. The filtrate and wash solutions were evaporated under vacuum; the residue was mixed with benzene, washed twice with 250 ml. portions of dilute aqueous sodium chloride, dried over $MgSO_4$, filtered, evaporated under vacuum and stripped with air. There was obtained 50.5 g. (95.1% of theoretical) of N,N-dimethyldithiocarbamyl acetone, $n_D^{30}$ 1.5962.

Then, 2.12 g. (0.02 mole) of this compound 2.9 g. (0.012 mole) ethyl, O-ethylphosphonodithioyl-S-acethydrazide, 100 ml. benzene and 10 ml. hexane were mixed and treated as in Example 5. There was obtained 4.71 g. (97.9% of theoretical) of the desired product, a viscous brown liquid, $n_D^{30}$ 1.6098. The structure of the compound was confirmed by nmr (nuclear magnetic resonance) analysis; which also indicated the purity of the product as being approximately 70–80%.

The following Table I contains some representative compounds of this invention:

TABLE I

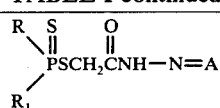

| Compound | R | $R_1$ | A | $n_D^{30}$ |
|---|---|---|---|---|
| 1 | $C_2H_5O$ | $C_2H_5O$ | $C(CH_3)_2$ | 1.5329 |
| 2 | $C_2H_5O$ | $C_2H_5O$ | $C(CH_3)(C_2H_5)$ | 1.5199 |
| 3 | $C_2H_5O$ | $C_2H_5O$ | $C(CH_3)(CH_2CH(CH_3)_2)$ | 1.5148 |
| 4 | $C_2H_5$ | $i-C_3H_7O$ | $C(CH_3)_2$ | 1.5392 |
| 5 | $C_2H_5$ | $i-C_3H_7O$ | $C(CH_3)(C_2H_5)$ | 1.5356 |
| 6 | $C_2H_5$ | $i-C_3H_7O$ | $C(CH_3)(CH_2CH(CH_3)_2)$ | 1.5246 |
| 7 | $C_2H_5$ | $i-C_3H_7O$ | $C(CH_3)(CH(CH_3)_2)$ | 1.5336 |
| 8 | $C_2H_5$ | $i-C_3H_7O$ | $C(CH_3)(C(CH_3)_3)$ | 1.5286 |
| 9 | $C_2H_5$ | $i-C_3H_7O$ | $C(CH_3)(C_6H_5)$ | 1.5822 |
| 10 | $C_2H_5$ | $C_2H_5O$ | $C(CH_3)_2$ | 1.5493 |
| 11 | $C_2H_5$ | $C_2H_5O$ | $C(CH_3)(C_2H_5)$ | 1.5406 |
| 12 | $C_2H_5$ | $C_2H_5O$ | $C(CH_3)(CH_2CH(CH_3)_2)$ | 1.5312 |
| 13 | $C_2H_5$ | $C_2H_5O$ | $C(CH_3)(CH(CH_3)_2)$ | 1.5336 |
| 14 | $C_2H_5$ | $C_2H_5O$ | $C(CH_3)(CH(CH_3)_3)$ | 1.5330 |
| 15 | $C_2H_5$ | $C_2H_5O$ | $C(CH_3)(C_6H_5)$ | 1.5946 |
| 16 | $C_2H_5O$ | $C_2H_5O$ | $C(CH_3)(CH(CH_3)_2)$ | 1.5200 |
| 17 | $C_2H_5O$ | $C_2H_5O$ | $C(CH_3)(C(CH_3)_3)$ | 1.5138 |
| 18 | $C_2H_5O$ | $C_2H_5O$ | $C(CH_3)(C_6H_5)$ | semi-solid |
| 19 | $C_2H_5O$ | $C_2H_5O$ | $C(CH_3)(CH_2CH_2C_6H_5)$ | 1.5484 |
| 20 | $C_2H_5$ | $C_2H_5O$ | $C(CH_3)(CH_2CH_2C_6H_5)$ | 1.5657 |
| 21 | $C_2H_5O$ | $C_2H_5O$ | $C(\text{cyclopropyl})(\text{cyclopropyl})$ | 1.5212 |
| 22 | $C_2H_5$ | $C_2H_5O$ | $C(\text{cyclopropyl})(\text{cyclopropyl})$ | 1.5206 |
| 23 | $C_2H_5$ | $C_2H_5O$ | $C(CH_3)(CH_2SC(S)N(CH_3)_2)$ | 1.6098 |
| 24 | $C_2H_5O$ | $C_2H_5O$ | $CHCH(CH_3)_2$ | 1.4950 |
| 25 | $C_2H_5O$ | $C_2H_5O$ | $CHCH_3$ | 1.5520 |
| 26 | $C_2H_5O$ | $C_2H_5O$ | cyclohexyl | 1.5436 |
| 27 | $C_2H_5$ | $i-C_3H_7O$ | cyclohexyl | 1.5506 |
| 28 | $C_2H_5$ | $C_2H_5O$ | cyclohexyl | 1.5563 |

TABLE I-continued

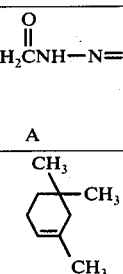

| Compound | R | $R_1$ | A | $n_D^{30}$ |
|---|---|---|---|---|
| 29 | $C_2H_5$ | $C_2H_5O$ | $CH_3$ ⟨benzene with 2 $CH_3$⟩ | 1.5534 |

Insecticidal Evaluation

The compounds in the foregoing Table I, were tested for insecticidal activity by the following procedures:

Housefly (*Musca domestica* L.):

Test compounds were diluted in acetone and aliquots pipetted onto the bottom of 55×15 mm. aluminum dishes. To insure even spreading of the chemical on the bottom of the dishes, 1 ml. of acetone containing 0.02% peanut oil was also added to each dish. After all solvents had evaporated, the dishes were placed in circular cardboard cages containing 25 female houseflies, 1–2 days old. The cages were covered on the bottom with cellophane and on the top with tulle netting, and each contained a sugar-water saturated cotton plug for maintenance of the flies. Mortality was recorded after 48 hours. Test levels ranged from 100 µg./25 female houseflies down to that at which approximately 50% mortality occurred. The $LD_{50}$ values are expressed below in Table II under heading "HF", in terms of µg. of the test compound per 25 female flies.

Black Bean Aphid [*Aphis fabae* (Scop.)]:

Nasturtium plants (*Tropaeolum sp.*) approximately 5 cm. tall, were transplanted into sandy loam soil in 3-inch clay pots and infested with 25–50 black bean aphids of mixed ages. 24 hours later, they were sprayed, to the point of runoff, with 50—50 acetone-water solutions of the test chemicals. Treated plants were held in the greenhouse and mortality was recorded after 7 days. Test concentrations ranged from 0.05% down to that at which 50% mortality occurred. $LD_{50}$ values are expressed below in Table II under the heading "BA" in terms of percent of the test compound in the sprayed solution.

Green Peach Aphid [*Myzus persicae* (Sulzer)]:

Radish plants (Rhaphanus sativus), approximately 2 cm. tall, were transplanted into sandy loam soil in 3-inch clay pots and infested with 25–50 green peach aphids of mixed ages. 24 hours later, they were sprayed, to the point of runoff, with 50—50 acetone-water solutions of the test chemicals. Treated plants were held in the greenhouse and mortality was recorded after 48 hours. Test concentrations ranged from 0.05% down to that at which 50% mortality occurred. $LD_{50}$ values are expressed below in Table II under the heading "GPA" in terms of percent of the test compound in the sprayed solution.

German Cockroach [*Blatella germanica* (Linn.)]:

Test compounds were diluted in a 50—50 acetone-water solution. 2 cc. of the solution were sprayed through a DeVilbiss type EGA hand spray gun into circular cardboard cages containing 10 one-month-old German coakroach nymphs. The test cages were covered on the bottom with cellophane and on the top with tulle netting. Percent mortality was recorded 7 days later. Test concentrations ranged from 0.1% down to that at which approximately 50% mortality occurred. $LD_{50}$ values are expressed below in Table II under the heading "GR" in terms of percent of the test compound in the sprayed solution.

Lygus Bug [*Lygus hesperus* (Knight)]:

Test compounds were diluted in a 50—50 acetone-water solution. 2 cc. of the solution were sprayed through a DeVilbiss type EGA hand spray gun into a circular cardboard cages containing 1 string bean pod and 10 adult lygus bugs. The test cages were covered on the bottom with cellophane and on the top with tulle netting. Percent mortality was recorded 48 hours later. Test concentrations ranged from 0.05% down to that at which approximately 50% mortality occurred. $LD_{50}$ values are expressed below in Table II under the heading "LB" in terms of percent of test compound in the sprayed solution.

Salt-Marsh Caterpillar [*Estigmene acrea* (Drury)]:

Test compounds were diluted in a 50—50 acetone-water solution. Sections of curly dock (Rumex crispus) leaves approximately 1 × 1.5 inches, were immersed in the test solution for 2 × 3 seconds and placed on a wire screen to dry. The dried leaves were placed in Petri dishes containing a moistened piece of filter paper and infested with 5 second-instar salt-marsh larvae. Mortality of the larvae was recorded 48 hours later, and a piece of synthetic media was added to dishes containing survivors. These then were held for 5 additional days to observe for any delayed effects of test chemicals.

Test concentrations ranged from 0.05% down to that at which approximately 50% mortality occurred. $LD_{50}$ values are expressed below in Table II under the heading "SMC" in terms of percent of the test compound in the solution.

Cabbage Looper [*Trichoplusia ni* (Hubner)]:

Test compounds were diluted in a 50—50 acetone-water solution. Cotyledons of hyzini squash (*Calabacita abobrinha*), approximately 1 × 1.5 inches, were immersed in the test solutions for 2–3 seconds and placed on a wire screen to dry. The dried leaves were placed in Petri dishes containing a moistened piece of filter paper and infested with five second-instar cabbage looper larvae. Mortality of the larvae was recorded 48 hours later, and a piece of synthetic media added to dishes containing survivors. These were then held for five additional days to observe for any delayed effects of the test chemicals.

Test concentrations ranged from 0.1% to that at which approximately 50% mortality occurred. $LD_{50}$ values are expressed below in Table II under the heading "CL" in terms of percent of the test compound in this solution.

Tobacco Budworm [*Heliothis virescens* (F.)]:

Test compounds were diluted in a 50—50 acetone-water solution. Sections of Romaine lettuce (*Latuca sativa*) leaves, approximately 1 × 1.5 inches, were immersed in the test solutions for 2–3 seconds and placed on a wire screen to dry. The dried leaves were placed in Petri dishes containing a moistened piece of filter paper and infested with five second-instar tobacco budwork larvae. Mortality of the larvae was recorded 48 hours later, and a piece of synthetic media added to dishes containing survivors. These were then held for five additional days to observe for any delayed effects of the test chemicals.

Test concentrations ranged form 0.1% to that at which approximately 50% mortality occurred. $LD_{50}$ values are expressed below in Table II under the heading "TBW" in terms of percent of the test compound in the solution.

Southern House Mosquito Larvae [*Culex pipiens quinquefasciatus Say*]:

Insecticidal activity was determined using third instar larvae of the mosquito *culex pipiens quinquefasciatus*. Ten larvae were placed in a six ounce, paper cup containing 100 ml. of an aqueous solution of the test chemical. The treated larvae were stored at 70° F. and 48 hours later the mortality was recorded. Test concentrations ranged from 0.5 ppm down to that at which approximately 50% mortality occurred. $LD_{50}$ values are expressed below in Table II under the heading "MOS" in terms of ppm of the test compound in the solution.

Acaricidal Evaluation

The compounds in Table I were tested for acaricidal activity according to the following procedure:

The two-spotted mite, *Tetranychus urticae* (Koch), was employed. The test procedure was as follows:

Pinto bean plants (*Phaseolus sp.*) approximately 10 cm. tall, were transplanted into sandy loam soil in 3-inch clay pots and thoroughly infested with two-spotted mites of mixed ages and sexes. 24 hours later, the infested plants were inverted and dipped for 2-3 seconds in 50—50 acetone-water solutions of the test chemicals. Treated plants were held in the greenhouse, and 7 days later mortality was determined for both the adult mites and the nymphs hatching from eggs which were on the plants at the time of treatment. Test concentrations ranged from 0.05% down to that at which 50% mortality occurred. $LD_{50}$ values are expressed below in Table II under the headings "2SM-PE" (i.e., post-embryonic) and "2SM-Eggs", in terms of percent concentration of the test compound in the solution.

Systemic Evaluation

The compounds in Table I were tested for systemic aphicidal activity according to the following procedures:

This test evaluates the root absorption and upward translocation of the candidate systemic compound. The Bean Aphid, *Aphis fabae* (Scop.) was employed in the test for systemic activity. Tests were conducted as follows:

Black Bean Aphid:

Test chemicals were diluted in acetone and aliquots thoroughly mixed into 500 grams of dry, sandy loam soil. The treated soil was placed in a pint-sized carton and a nasturtium plant (*Tropaeolum sp.*) approximately 5 cm. tall was transplanted into each carton. The plants were then infested with approximately 25 black bean aphids of mixed ages and placed in the greenhouse. 7 days later mortality was recorded. Test concentrations ranged from 10 ppm down to that at which approximately 50% mortality occurred.

$LD_{50}$ values are expressed below in Table II under the heading "BA(S)", in terms of percent concentration of the test compound.

Green Peach Aphid:

Tests were similarly conducted using the compounds in Table I with the exception that radish plants (*Rhaphanus sativus*) 2 cm. tall were used. The results are reported in Table II under the heading "GPA-(s)".

TABLE II

| Compound No. | HF, μg. | BA, % | BA(S), ppm | GPA, % | GPA(S), ppm | GR, % | LB, % | SMC, % | CL, % | TBW, % | MOS, ppm | 2-SM PE, % | 2-SM EGGS, % |
|---|---|---|---|---|---|---|---|---|---|---|---|---|---|
| 1 | >100 | 0.05 | >10 | — | — | >0.1 | >0.05 | 0.05 | — | — | >1 | 0.05 | <0.05 |
| 2 | 75 | 0.005 | >10 | >0.05 | — | >0.1 | >0.05 | >0.05 | >0.1 | >0.1 | >1 | <0.05 | >0.05 |
| 3 | 34 | 0.002 | >10 | 0.03 | — | >0.1 | >0.05 | >0.05 | >0.1 | >0.1 | >1 | <0.05 | <0.05 |
| 4 | 23 | 0.0005 | 5 | 0.002 | >10 | >0.1 | >0.05 | 0.05 | >0.1 | 0.1 | >1 | <0.05 | <0.05 |
| 5 | 20 | 0.0005 | 5 | 0.005 | >10 | >0.1 | 0.05 | >0.05 | >0.1 | >0.1 | >1 | <0.05 | <0.05 |
| 6 | 20 | 0.0002 | 5 | 0.002 | 10 | >0.1 | 0.03 | >0.05 | >0.1 | 0.1 | >1 | <0.05 | <0.05 |
| 7 | 22 | 0.0003 | >10 | 0.003 | >10 | >0.1 | >0.05 | >0.05 | >0.1 | >0.1 | >1 | <0.05 | <0.05 |
| 8 | 21 | 0.0002 | >10 | 0.002 | >10 | >0.1 | >0.05 | >0.05 | >0.1 | 0.1 | 1 | <0.05 | <0.05 |
| 9 | 29 | 0.0003 | >10 | 0.001 | >10 | >0.1 | >0.05 | >0.05 | >0.1 | >0.1 | 1 | <0.05 | <0.05 |
| 10 | 29 | 0.002 | >10 | 0.005 | >10 | >0.1 | >0.05 | >0.05 | >0.1 | >0.1 | 0.3 | <0.05 | <0.05 |
| 11 | 28 | 0.002 | >10 | 0.005 | >10 | >0.1 | >0.05 | >0.05 | >0.1 | >0.1 | 1 | <0.05 | <0.05 |
| 12 | 28 | 0.001 | >10 | 0.002 | >10 | >0.1 | >0.05 | >0.05 | >0.1 | >0.1 | 0.4 | <0.05 | <0.05 |
| 13 | 30 | 0.001 | >10 | 0.002 | >10 | >0.1 | >0.05 | >0.05 | >0.1 | >0.1 | 0.4 | <0.05 | <0.05 |
| 14 | 30 | 0.0005 | >10 | 0.005 | >10 | >0.1 | 0.05 | >0.05 | >0.1 | >0.1 | 0.3 | <0.05 | <0.05 |
| 15 | 29 | 0.001 | >10 | 0.003 | >10S | >0.1 | >0.05 | 0.05 | >0.1 | >0.1 | 0.8 | <0.05 | <0.05 |
| 16 | >100 | 0.03 | >10 | — | — | — | — | >0.05 | — | — | >1 | <0.05 | <0.05 |
| 17 | 50 | 0.01 | >10 | >0.05 | — | >0.1 | >0.05 | >0.05 | >0.1 | >0.1 | >1 | <0.05 | <0.05 |
| 18 | 84 | 0.005 | >10 | 0.03 | — | >0.1 | >0.05 | >0.05 | >0.1 | >0.1 | >1 | <0.05 | <0.05 |
| 19 | 79 | 0.03 | >10 | 0.01 | >10 | >0.1 | >0.05 | >0.05 | >0.1 | >0.1 | >1 | <0.05 | <0.05 |
| 20 | 79 | 0.002 | >10 | 0.03 | >10 | >0.1 | >0.05 | >0.05 | >0.1 | >0.1 | 0.8 | <0.05 | <0.05 |
| 21 | 35 | 0.03 | >10 | >0.05 | >10 | >0.1 | >0.05 | >0.05 | >0.1 | >0.1 | >1 | <0.05 | <0.05 |
| 22 | 25 | 0.002 | >10 | 0.002 | >10 | >0.1 | >0.05 | >0.05 | >0.1 | >0.1 | >1 | <0.05 | <0.05 |
| 23 | 32 | >0.05 | — | — | — | >0.1 | >0.05 | >0.05 | >0.1 | >0.1 | 0.05 | >0.05 | <0.05 |
| 24 | >100 | >0.05 | — | — | — | >0.1 | >0.05 | >0.05 | — | — | >1 | >0.05 | <0.05 |
| 25 | >100 | >0.05 | — | — | — | >0.1 | >0.05 | >0.05 | — | — | >1 | <0.05 | <0.05 |
| 26 | 100 | 0.005 | >10 | >0.05 | — | >0.1 | >0.05 | >0.05 | >0.1 | >0.1 | >1 | <0.05 | <0.05 |
| 27 | 30 | 0.002 | >10 | 0.005 | >10 | >0.1 | 0.05 | >0.05 | >0.1 | >0.1 | >1 | <0.05 | <0.05 |
| 28 | 29 | 0.003 | >10 | 0.005 | >10 | >0.1 | >0.05 | >0.05 | >0.1 | >0.1 | >1 | <0.05 | <0.05 |
| 29 | 91 | >0.05 | — | — | — | >0.1 | 0.05 | >0.05 | >0.1 | >0.1 | 0.4 | >0.05 | >0.05 |

The compounds of this invention are generally embodied into a form suitable for convenient application. For example, the compounds can be embodied into pesticidal compositions which are provided in the form of emulsions, suspensions, solutions, dusts, and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions using compounds of this invention can contain, as adjuvants, organic solvents, such as sesame oil, xylene range solvents, heavy petroleum, etc.; water, emulsifying agents, surface active agents, talc, prophyllite, diatomite, gypsum, clays, propellants, such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when compound is ingested into the body of the pest.

The precise manner in which the pesticidal compositions using compounds of this invention are used in any particular instance will be readily apparent to a person skilled in the art. Generally, the active compound will be embodied in the form of a liquid composition; for example, an emulsion, suspension, or aerosol spray. While concentration of the active compound in the present composition can vary within rather wide limits, ordinarily the compound will comprise between about 0.01 and about 80% by weight of the composition.

What is claimed is:

1. A method of combatting insects comprising applying to the insect or the habitat thereof an insecticidally effective amount of a compound having the formula

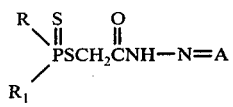

in which R is lower alkyl or lower alkoxy; $R_1$ is lower alkoxy; A is cycloalkyl, lower alkyl-substituted cycloalkenyl or

$R_2$ is alkyl, aryl, aralkyl, cycloalkyl, hydrogen or

$R_3$ is aryl, aralkyl, cycloalkyl or

and $R_4$ is lower alkyl.

2. An insecticidal composition of matter comprising:
(a) An insecticidally effective amount of a compound having the formula

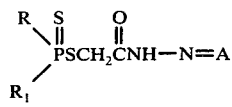

in which R is lower alkyl or lower alkoxy; $R_1$ is lower alkoxy; A is cycloalkyl, lower alkyl-substituted cycloalkenyl or

$R_2$ is alkyl, aryl, aralkyl, cycloalkyl, hydrogen or

$R_3$ is aryl, aralkyl, cycloalkyl or

and $R_4$ is lower alkyl; and
(b) an inert carrier.

3. A compound having the formula

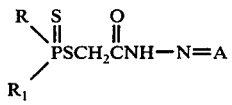

in which R is lower alkyl or lower alkoxy; $R_1$ is lower alkoxy; A is cycloalkyl, lower alkyl-substituted cycloalkenyl or

$R_2$ is alkyl, aryl, aralkyl, cycloalkyl, hydrogen or

$R_3$ is aryl, aralkyl, cycloalkyl or

and $R_4$ is lower alkyl.

4. A method according to claim 1 in which R is lower alkyl and $R_1$ is lower alkoxy.

5. A method according to claim 1 in which R is lower alkoxy and $R_1$ is lower alkoxy.

6. A method according to claim 1 in which R is ethyl, $R_1$ is isopropoxy, A is

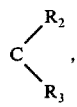

$R_2$ is methyl and $R_3$ is phenyl.

7. A method according to claim 1 in which R is ethyl, $R_1$ is ethoxy, A is

$R_2$ is methyl and $R_3$ is phenyl.

8. A method according to claim 1 in which R is ethyl, $R_1$ is ethoxy, A is

$R_2$ is methyl and $R_3$ is phenethyl.

9. A method according to claim 1 in which R is ethyl, $R_1$ is ethoxy, A is

$R_2$ is methyl and $R_3$ is $$CH_2S\overset{\overset{S}{\|}}{C}N(R_4)_2.$$

10. A method according to claim 1 in which R is ethyl, $R_1$ is ethoxy, and A is 3,5,5-trimethylcyclohex-2-enyl.

11. A method according to claim 1 in which A is

$R_2$ is alkyl and $R_3$ is phenyl.

12. A compound according to claim 3 in which R is lower alkyl and $R_1$ is lower alkoxy.

13. A compound according to claim 3 in which R and $R_1$ are both lower alkoxy.

14. A compound according to claim 3 in which A is

$R_2$ is alkyl and $R_3$ is phenyl.

15. A compound according to claim 3 in which R is ethyl, $R_1$ is isopropoxy, A is

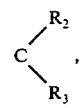

$R_2$ is methyl and $R_3$ is phenyl.

16. A compound according to claim 3 in which R is ethyl, $R_1$ is ethoxy, A is

$R_2$ is methyl and $R_3$ is phenyl.

17. A compound according to claim 3 in which R and $R_1$ are both ethoxy, A is

$R_2$ is methyl and $R_3$ is phenyl.

18. A compound according to claim 3 in which R and $R_1$ are both ethoxy, A is

$R_2$ is methyl and $R_3$ is phenethyl.

19. A compound according to claim 3 in which R is ethyl, $R_1$ is ethoxy, A is

$R_2$ is methyl and $R_3$ is phenethyl.

20. A compound according to claim 3 in which R and $R_1$ are both ethoxy, A is and $R_2$ and $R_3$ are both cyclopropyl.

21. A compound according to claim 3 in which R is ethyl, $R_1$ is ethoxy, A is

and $R_2$ and $R_3$ are both cyclopropyl.

22. A compound according to claim 3 in which R is ethyl, $R_1$ is ethoxy, A is $R_2$ is methyl and $R_3$ is

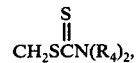

and $R_4$ is methyl.

23. A compound according to claim 3 in which R and $R_1$ are both ethoxy and A is cyclohexyl.

24. A compound according to claim 3 in which R is ethyl, $R_1$ is isopropoxy and A is cyclohexyl.

25. A compound according to claim 3 in which R is ethyl, $R_1$ is ethoxy and A is cyclohexyl.

26. A compound according to claim 3 in which R is ethyl, $R_1$ is ethoxy and A is 3,5,5-trimethylcyclohex-2-enyl.

* * * * *